(12) United States Patent
Foody et al.

(10) Patent No.: US 7,754,457 B2
(45) Date of Patent: Jul. 13, 2010

(54) METHOD OF CONTINUOUS PROCESSING OF LIGNOCELLULOSIC FEEDSTOCK

(75) Inventors: Brian Foody, Ontario (CA); Jeffrey S. Tolan, Ontario (CA)

(73) Assignee: Iogen Energy Corporation, Ontario (CA)

( * ) Notice: Subject to any disclaimer, the term of this patent is extended or adjusted under 35 U.S.C. 154(b) by 353 days.

(21) Appl. No.: 11/916,347

(22) PCT Filed: Jun. 2, 2006

(86) PCT No.: PCT/CA2006/000910

§ 371 (c)(1),
(2), (4) Date: Jan. 28, 2008

(87) PCT Pub. No.: WO2006/128304

PCT Pub. Date: Dec. 7, 2006

(65) Prior Publication Data

US 2008/0293114 A1 Nov. 27, 2008

Related U.S. Application Data

(60) Provisional application No. 60/687,224, filed on Jun. 3, 2005.

(51) Int. Cl.
*C12P 7/08* (2006.01)
*C12P 7/10* (2006.01)
*C12P 19/04* (2006.01)

(52) U.S. Cl. .......................... 435/165; 127/37; 435/72; 435/99; 435/101; 435/105; 435/161; 435/163; 536/124; 536/128

(58) Field of Classification Search .................. None
See application file for complete search history.

(56) References Cited

U.S. PATENT DOCUMENTS

| 4,342,831 | A * | 8/1982 | Faber et al. .................. 435/163 |
| 4,908,067 | A * | 3/1990 | Just .............................. 127/37 |
| 5,366,558 | A * | 11/1994 | Brink ........................... 127/43 |
| 5,628,830 | A * | 5/1997 | Brink ........................... 127/36 |
| 7,198,925 | B2 * | 4/2007 | Foody .......................... 435/105 |
| 7,585,652 | B2 * | 9/2009 | Foody et al. ................. 435/163 |
| 2006/0068475 | A1 * | 3/2006 | Foody .......................... 435/105 |
| 2007/0148751 | A1 * | 6/2007 | Griffin et al. ................. 435/161 |

FOREIGN PATENT DOCUMENTS

WO 2006/007691 1/2006

OTHER PUBLICATIONS

Yamada, et al., "Performance of Immobilized Zymomonas mobilitis 31821 (pZB5) on Actual Hydrolysates Produced by . . . ", Applied Biochemistry and Biotechnology, vol. 98-100 (2002) 899-907.

* cited by examiner

*Primary Examiner*—Herbert J. Lilling
(74) *Attorney, Agent, or Firm*—Fitzpatrick, Cella, Harper & Scinto

(57) ABSTRACT

A continuous process for treating a lignocellulosic feedstock is provided. This method comprises pretreating the lignocellulosic feedstock under pressure in a pretreatment reactor at a pH between about 0.4 and about 2.0. One or more than one soluble base is added to this pressurized, pretreated feedstock after it exits the pretreatment reactor to adjust the pretreated lignocellulosic feedstock to an intermediate pH of between about pH 2.5 to about pH 3.5. This pressurized, partially-neutralized feedstock is then further processed at the intermediate pH. This may include flashing one or more than one time at the intermediate pH. The pH of the pressurized, partially-neutralized feedstock may then be adjusted with one or more than one base to produce a neutralized feedstock having a pH between about 4 and about 6. Prior to adjusting the pH to between about 2.5 and about 3.5, the pressurized, pretreated feedstock truly be partially depressurized.

31 Claims, 2 Drawing Sheets

METHOD OF CONTINUOUS PROCESSING OF LIGNOCELLULOSIC FEEDSTOCK

FIELD OF INVENTION

The present invention relates to a method for continuous processing of lignocellulosic feedstocks. More specifically, the present invention relates to a method of continuous processing of lignocellulosic feedstocks using acidic pretreatment.

BACKGROUND OF THE INVENTION

Fuel ethanol is currently made from feedstocks such as corn starch, sugar cane, and sugar beets. The production of ethanol from these sources cannot increase much further as most of the farmland suitable for the production of these crops is in use. Also, these feedstocks can be costly since they compete with the human and animal food chain. Finally, the use of these feedstocks has a negative impact on the environment because the use of fossil fuels in the conversion process releases carbon dioxide and other byproducts.

The production of fuel ethanol from cellulosic feedstocks provides an attractive alternative to the fuel ethanol feedstocks used to date. Cellulose is the most abundant natural polymer, so there is an enormous untapped potential for its use as a source of ethanol. Also, cellulosic feedstocks to be used for ethanol production are inexpensive as they have limited use. Another advantage of these feedstocks is that lignin, which is a byproduct of the cellulose conversion process, can be used as a fuel to power the conversion process, thereby avoiding the use of fossil fuels. Several studies have concluded that, when the entire production and consumption cycle is taken into account, the use of ethanol produced from cellulose generates close to nil greenhouse gases.

The cellulosic feedstocks that are the most promising for ethanol production include (1) agricultural wastes such as corn stover, corn cobs, corn fiber, wheat straw, barley straw, oat straw, oat hulls, rice straw, rice hulls, canola straw, and soybean stover; (2) grasses such as switch grass, miscanthus, cord grass, rye grass and reed canary grass; (3) forestry biomass such as recycled wood pulp fiber, softwood, hardwood and sawdust; and (4) sugar processing residues such as bagasse and beet pulp.

The first step of the conversion process involves handling and possibly size reduction of the material. The feedstock must be conveyed into the plant. This may be carried out by trucks, followed by placing the feedstock on conveyors. The feedstock particle size may be reduced prior to the subsequent processing steps.

The two primary cellulose hydrolysis processes are acid hydrolysis and enzymatic hydrolysis.

In the acid hydrolysis process, the feedstock is subjected to steam and a strong acid, such as sulfuric acid, at a temperature, acid concentration and length of time that are sufficient to hydrolyze the cellulose to glucose and hemicellulose to xylose and arabinose. In the case when sulfuric acid is used, the acid can be concentrated (25-80% w/w) or dilute (3-8% w/w), measured as the weight of acid in the weight of acidified aqueous solution that is present with the feedstock. The glucose is then fermented to ethanol using yeast, and the ethanol is recovered and purified by distillation.

In the enzymatic hydrolysis process, the combination of steam temperature, acid concentration and treatment time are chosen to be milder than that in the acid hydrolysis process such that the cellulose surface area is greatly increased as the fibrous feedstock is converted to a muddy texture, but there is little conversion of the cellulose to glucose. This steam/acid step is known as pretreatment. The cellulose is hydrolyzed to glucose in a subsequent step that uses cellulase enzymes. Prior to the addition of enzyme, the pH of the acidic feedstock is adjusted to a value that is suitable for the enzymatic hydrolysis reaction. Typically, this involves the addition of alkali to a pH of between about 4 to about 6, which is the optimal pH range for cellulases, although the pH can be higher if alkalophilic cellulases are used.

In the enzymatic hydrolysis process, the addition of an acid, such as 0.1% to 2% (w/w) sulfuric acid to the pretreatment step improves the digestion of the cellulose and shortens the time for pretreatment. As used herein, unless otherwise specifically indicated, the unit of acid concentration in the pretreatment expressed as % w/w means the percentage weight of pure acid in the total weight of dry feedstock plus aqueous solution. Achieving and maintaining these conditions requires a highly acid-resistant system. The early work in the field focused on the use of batch pretreatment reactors, which are well suited for handling the acid and can have high pressure steam added to them rapidly. In one type of batch system, the pressure is brought down rapidly with explosive decompression, which is known as steam explosion. Foody, (U.S. Pat. No. 4,461,648) describes the equipment and conditions used in steam explosion pretreatment. Steam explosion with sulfuric acid added to achieve a pH of 0.4 to 2.0 has been the standard pretreatment process for two decades. It produces pretreated material that is uniform and requires less cellulase enzyme to hydrolyze cellulose than other pretreatment processes.

Steam explosion and other batch pretreatment processes produce feedstocks with highly accessible cellulose. However, batch processes have inherently lower throughput than continuous processes due to the time required for loading, heat-up, cool-down and unloading the reactor. The low throughput greatly increases the number of steam pretreatment reactors required, which is costly and makes the system difficult to operate. Another disadvantage associated with batch pretreatment, in particular steam explosion, is the difficulty in recovering and reusing the steam. The steam requirement to achieve and maintain the feedstock pretreatment conditions is high. The loss of this steam after a single treatment reaction represents a significant cost in the ethanol production process.

The development of a continuous acid pretreatment process that can be operated and maintained economically has been the goal of various researchers in the field. One factor that reduces the economic feasibility of these processes is that the process equipment downstream of the pretreatment reactor, such as flash tanks, are exposed to the acidic, pretreated feedstock, which is typically at a pH of about 0.4 to 2.0. To prevent corrosion of the equipment due to exposure to such low pH values, the exposed equipment parts would typically be constructed of an acid-resistant material, such as zirconium, which adds considerable expense. Furthermore, the sugars present in the pretreated feedstock (e.g., glucose, xylose and arabinose) degrade under acidic conditions, which is exacerbated by localized areas of low pH that may be present in the feedstock.

Another factor that has hindered the development of continuous processes that utilize acid pretreatment is that equipment downstream of the pretreatment reactor is prone to the build up and deposition of insoluble salts known as "scale". The addition of sulfuric acid to the feedstock during pretreatment forms mixtures of sulfuric acid, bisulfate salts and sulfate salts. Analogous salts are formed with the use of other acids, e.g. sulfite and bisulfite salts form after the addition of sulfurous acid. The subsequent addition of alkali after exit of the acidified feedstock from the pretreatment reactor to increase the pH to a value suitable for enzyme hydrolysis (typically between pH 4 and 6), or for sugar fermentation in the case of acid hydrolysis, increases the concentration of sulfate and bisulfate salts when sulfuric acid is used in pretreatment. When combined with the calcium that is indigenous to the feedstock, the result of this increase in sulfate and bisulfate salts is the formation of calcium sulfate and calcium bisulfate. These insoluble salts tend to deposit as scale on the process equipment downstream of the point of addition of the alkali. Scale deposition can plug valves and retard the flow of the slurries. To compensate, equipment pumps must increase their output, which increases the energy requirements of the system as well as wear and tear on the pumps. In an extreme case, scale deposition can shut down a plant. Another problem of scale build-up is that it decreases heat transfer through piping. Each of these factors contributes to a reduction of the economics of the process. Although it is possible to remove the scale by washing with acid, this is a costly and time consuming process.

It is also desirable to remove volatile organic acids from the pretreated feedstock as these can inhibit the efficiency of downstream processes, such as enzyme hydrolysis and fermentation.

Various groups have investigated continuous pretreatment systems utilizing acid hydrolysis without a subsequent step of enzyme hydrolysis. For example, Just (U.S. Pat. No. 4,908,067) discloses a continuous process for the acid hydrolysis of wood or wood products. The system uses an acid soak stage and the feedstock is then sent through several reactors, each of which provides for a co-current washing of the material. This combined reactor/washing system is a much more complicated system than that envisioned for pretreatment prior to enzyme hydrolysis. Furthermore, due to the use of concentrated acid, the process equipment would need to be acid-resistant, which, as set out above, adds considerable expense.

Brink (U.S. Pat. No. 5,366,558) describes a continuous acid hydrolysis process that occurs in several stages. The first stage is an acid hydrolysis step carried out at a pH of about 1.4 to 3.0, and a temperature of about 140° C. to 220° C., followed by mechanical disintegration to particles of a very small size and sensitization with oxygen. The sensitized material is then subjected to a final hydrolysis reaction at a pH of about 1.2 to 2.5 and a temperature of about 160° C. to 240° C. The material is washed counter-currently and a sugar stream and lignin are the products. A disadvantage of this process is that it is much more complex than a pretreatment prior to enzymatic hydrolysis. The process also runs the risk of severe degradation of reaction products with the multiple reaction steps at high temperature and pressure. Furthermore, process equipment downstream of acid addition would be exposed to the harshly acidic feedstock.

Faber et al. (U.S. Pat. No. 4,342,831) disclose a process that involves acid hydrolysis of lignocellulosic material at pH 0.5 to 1.5 to produce a hydrolyzate. The hydrolyzate is then subjected to an abrupt depressurization (which is flashing or venting) in which a fraction of the hydrolyzate vaporizes and may be recovered. The depressurized hydrolyzate, having a pH of about 0.5 to 1.5, is then optionally partially neutralized by adjusting its pH to 4.0 with limestone or ammonium hydroxide to reduce corrosion in subsequent processing. This step of partial neutralization necessitates an additional filtration step to remove precipitated material. The hydrolyzate is subsequently steam-stripped at 95-105° C. (which corresponds to atmospheric pressure) to remove furfural and other volatile products and the pH adjusted to 10.5 with calcium oxide to degrade 5-hydroxymethylfurfural (HMF). After filtration to remove precipitates, the hydrolyzate liquor is adjusted to pH 5.5-6.5 with phosphoric acid to precipitate more material, which is removed by filtration to produce a glucose stream.

Although Faber et al. disclose that a partial neutralization prior to steam-stripping is desirable to reduce corrosion during and after steam stripping, the depressurization step is carried out at a pH of 0.5-1.5 and thus the acidic, depressurized feedstock would be exposed to tanks and other equipment prior to the pH adjustment to 4.0. This necessitates that the tanks and other process equipment exposed to the harshly acidic feedstock be made of an acid-resistant material, which is costly. Furthermore, the process of Faber et al. results in high levels of xylose degradation, as indicated by the high levels of furfural production. It is preferable that minimal xylose degradation occurs. Another disadvantage of the process is that installing equipment for steam stripping and running a steam-stripping operation is costly and adds to the complexity of the process. Moreover, by adjusting the pH to 4, the efficiency of organic acid removal in the steam stripping step will be reduced.

Various groups have investigated continuous acid pretreatment systems followed by a subsequent step of enzyme hydrolysis. For example, Brink (U.S. Pat. No. 5,628,830) teaches a steam pretreatment followed by multiple flashes for steam recovery. However, this process handles the feedstock at a moisture content that is too low to allow the material to be pumped into the pretreatment reactor. This limits feedstock processing to dropping it into a hopper prior to pretreatment. The feedstock cannot be presoaked in dilute acid, as is practiced by Foody (supra), or leached, according to a method described by Griffin et al. (WO 02/070753). Moreover, the pretreatment process of Brink involves the addition of sulfuric acid at a point in the process such that acid is present in the heat exchanger, the recycle line, the pretreatment hydrolyzer, the disintegrator, the pretreatment pump, the flash tanks and the orifices. This requires all of these pieces of equipment to be resistant to corrosion by sulfuric acid.

Grethlein (U.S. Pat. No. 4,237,226) teaches a continuous pretreatment system to enhance the enzymatic or acid hydrolysis of cellulose in oak wood chips. Grethlein produces a slurry of wood chips to achieve 5% to 10% solids. The slurry is heated and then injected with a concentrated stream of sulfuric acid to reach a final acid concentration of 0 to 1% in the aqueous phase. Alternatively, the acid is added to the cellulose slurry first and then heated with live steam. The reaction is quenched by rapid cooling by flashing across an orifice or capillary at the outlet to the reactor. Grethlein's system does not address several issues with regard to a practical, continuous pretreatment process. For example, the use of an acid soak adds an additional process step, which increases the cost and complexity of the process. The acid soak may be avoided with a slow heat-up by a heat exchanger, but this is not suitable for a slurry with a high solids content. Furthermore, Grethlein's process results in the production of a harshly acidic feedstock during pretreatment that is exposed to flash tanks and other process equipment. Grethlein's process also does not address the build up of scale on process equipment.

Converse et al. (U.S. Pat. No. 4,556,430) followed Grethlein's work with the inclusion of a non-aqueous carrier in the feedstock system to decrease the amount of water present. The system does not address rapid acidification and heat-up, and the non-aqueous carrier must be handled and recovered in order for the process to be economical. Furthermore, as with Grethlein, the process of Converse would require acid resistant flash tanks and the process does not address build up of scale.

Therefore, there has not been a continuous, dilute acid pretreatment system reported that addresses the issues required for an economical commercial process. The development of such a system remains a critical requirement for a process to convert cellulose to glucose and subsequently to ethanol.

SUMMARY OF THE INVENTION

The present invention relates to a continuous process for treating a lignocellulosic feedstock. More specifically, the present invention provides a method for the continuous processing of lignocellulosic feedstocks by acidic pretreatment.

It is an object of the invention to provide an improved method for the treatment of lignocellulosic feedstocks.

According to the present invention, there is provided a method (A) for continuous processing of a lignocellulosic feedstock comprising the steps of:

a. pretreating the lignocellulosic feedstock at elevated pressure in a pretreatment reactor at a pH between about 0.4 and about 2.0 to produce a pressurized, pretreated feedstock;

b. adding one or more than one soluble base to the pressurized, pretreated feedstock after exit from the pretreatment reactor to adjust the pressurized, pretreated feedstock to an intermediate pH of between about pH 2.5 and about pH 3.5 to produce a pressurized, partially-neutralized feedstock;

c. flashing the pressurized, partially-neutralized feedstock one or more than one time at the intermediate pH to produce a flashed feedstock; and d. adjusting the pH of the flashed feedstock with one or more than one base to produce a neutralized feedstock having a pH between about 4 and about 6.

The lignocellulosic feedstock used in the process may be selected from the group consisting of wheat straw, barley straw, corn stover, soybean stover, canola straw, oat straw, rice straw, switch grass, cord grass, miscanthus and reed canary grass.

The present invention also pertains to the method (A) as described above, wherein, prior to the step of pretreating (step a.), the lignocellulosic feedstock is slurried to produce a feedstock slurry having a solids content of about 4-32% (w/w). The feedstock slurry may be prepared in water or in a mixture of water and a liquid that is immiscible or miscible with water.

The present invention also pertains to the method (A) as described above, wherein the step of pretreating (step a.) comprises pumping the lignocellulosic feedstock through the pretreatment reactor and heating the lignocellulosic feedstock to a temperature between about 160° C. and about 280° C. with steam for a time sufficient to hydrolyze at least a portion of the cellulose in the feedstock to produce glucose and at least a portion of the hemicellulose in the feedstock to produce a sugar monomer selected from the group consisting of xylose, arabinose, mannose, galactose and a combination thereof. The pretreating step (step a.) may be performed at a pressure between about 50 and about 700 psig or between about 75 and about 600 psig.

The present invention also pertains to the method (A) as described above wherein, prior to the step of pretreating (step a.), one or more than one acid selected from the group consisting of sulfuric acid, sulfurous acid, sulfur dioxide and a mixture thereof is added to the lignocellulosic feedstock. Preferably, the acid is sulfuric acid.

The present invention also pertains to the method (A) as described above, wherein prior to the step of adding the soluble base (step b.) and after the step of pretreating (step a.), the pressurized, pretreated feedstock is partially depressurized. The pressurized, pretreated feedstock may be partially depressurized by one or more than one flashing step.

The present invention also pertains to the method (A) as described above, wherein, in the step of adding the soluble base (step b.), the one or more than one soluble base is selected from the group consisting of ammonia, ammonium hydroxide, potassium hydroxide, sodium hydroxide, potassium carbonate, potassium bicarbonate, sodium carbonate, sodium bicarbonate and a mixture thereof. The one or more than one soluble base may be selected from the group consisting of ammonia, ammonium hydroxide and sodium hydroxide. Preferably, the soluble base is ammonia.

The present invention also pertains to the method (A) as described above, wherein, in the step of flashing (step c.), the flashed feedstock is at a temperature of between about 40° C. and about 125° C. Preferably, the flashed feedstock is at a temperature of between about 40° C. and about 100° C., or at a temperature of between about 50° C. and about 90° C.

In the step of flashing (step c.), the steam may be flashed to produce flashed steam and a portion of the flashed steam may be recovered.

The present invention also pertains to the method (A) as described above, wherein, in the step of adjusting (step d.), the pH of the neutralized feedstock is adjusted to between about pH 4.0 and about pH 5.5. Preferably, the pH of the neutralized feedstock is adjusted to between about pH 4.5 and about pH 5.5.

The present invention also pertains to the method (A) as described above, wherein, in the step of adjusting (step d.), the one or more than one base is selected from the group consisting of ammonia, ammonium hydroxide, lime, calcium hydroxide, potassium hydroxide, magnesium hydroxide, sodium hydroxide, potassium carbonate, potassium bicarbonate, sodium carbonate, sodium bicarbonate and a mixture thereof. Preferably, in the step of adjusting (step d.), the one or more than one base is a soluble base. Preferably, the one or more than one base is selected from the group consisting of ammonia, ammonium hydroxide and sodium hydroxide. The pH of the neutralized feedstock may be adjusted with the soluble base to between about 4.0 and about 5.5.

The present invention also pertains to the method (A) as described above, further comprising the steps of:

e. enzymatically hydrolyzing the neutralized feedstock produced in step d. to produce a sugar stream; and f. fermenting the sugar stream to produce ethanol.

According to the present invention, there is also provided a continuous process (B) for providing a processed lignocellulosic feedstock comprising the steps of:

a. pretreating a lignocellulosic feedstock at elevated pressure in a pretreatment reactor at a pH between about 0.4 and about 2.0 to produce a pressurized, pretreated lignocellulosic feedstock;

b. adding one or more than one soluble base to the pressurized, pretreated lignocellulosic feedstock after exit from the pretreatment reactor to adjust the pressurized, pretreated lignocellulosic feedstock to an intermediate pH of between about pH 2.5 to about pH 3.5 to produce a pressurized, partially-neutralized feedstock; and c. further processing the pressurized, partially-neutralized feedstock at the intermediate pH to produce the processed lignocellulosic feedstock.

The present invention also pertains to the process (B) as described above, wherein the step of further processing (step c.) comprises flashing or venting the pressurized, partially-neutralized feedstock.

The present invention also pertains to the process (B) as described above, wherein prior to the step of adding (step b.) and after the step of pretreating (step a.), the pressurized, pretreated feedstock is partially depressurized. The pressurized, pretreated feedstock may be partially depressurized by a flashing step.

The present invention also pertains to the process (B) as described above, wherein the step of pretreating (step a.) comprises pumping the lignocellulosic feedstock through the pretreatment reactor and heating the lignocellulosic feedstock to a temperature between about 160° C. and about 280° C. with steam for a time sufficient to hydrolyze at least a portion of cellulose in the feedstock to produce glucose and at least a portion of hemicellulose in the feedstock to produce a sugar monomer selected from the group consisting of xylose, arabinose, mannose, galactose and a combination thereof. The present invention also pertains to the process (B) as described above, wherein the pretreating step (step a.) is performed at a pressure between about 50 and about 700 psig or between about 75 and about 600 psig.

The processes of the present invention overcome several disadvantages of the prior art by taking into account the difficulties encountered in steps carried out during the conversion of lignocellulosic feedstock to sugar and then fermentation products such as ethanol. By adjusting the pH of the feedstock after pretreatment or after partial depressurization, and before further processing to an intermediate pH of between about 2.5 and about 3.5, the amount of downstream equipment exposed to the harshly acidic feedstock is minimized. A further advantage of adjusting the feedstock to an intermediate pH of about 2.5 to about 3.5 is that there is a reduction of scale deposition on process equipment in relation to treatment not utilizing this partial neutralization step. Furthermore, sugars such as glucose, xylose and arabinose present after pretreatment are more stable at this intermediate pH range than they would be if the feedstock was not adjusted to this intermediate pH range. Moreover, by carrying out an intermediate pH adjustment, the small amounts of base required make it easier to dispense evenly and avoids sugar degradation at localized areas of high pH.

An additional advantage is that, when a flashing step is carried out at the intermediate pH, the removal or recovery of volatile acids can still be carried out effectively. With pH adjustment directly to the neutralized pH of 4.0 to 6.0, such a flashing step would be less effective due to the formation of salts at pH values above 4.0.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
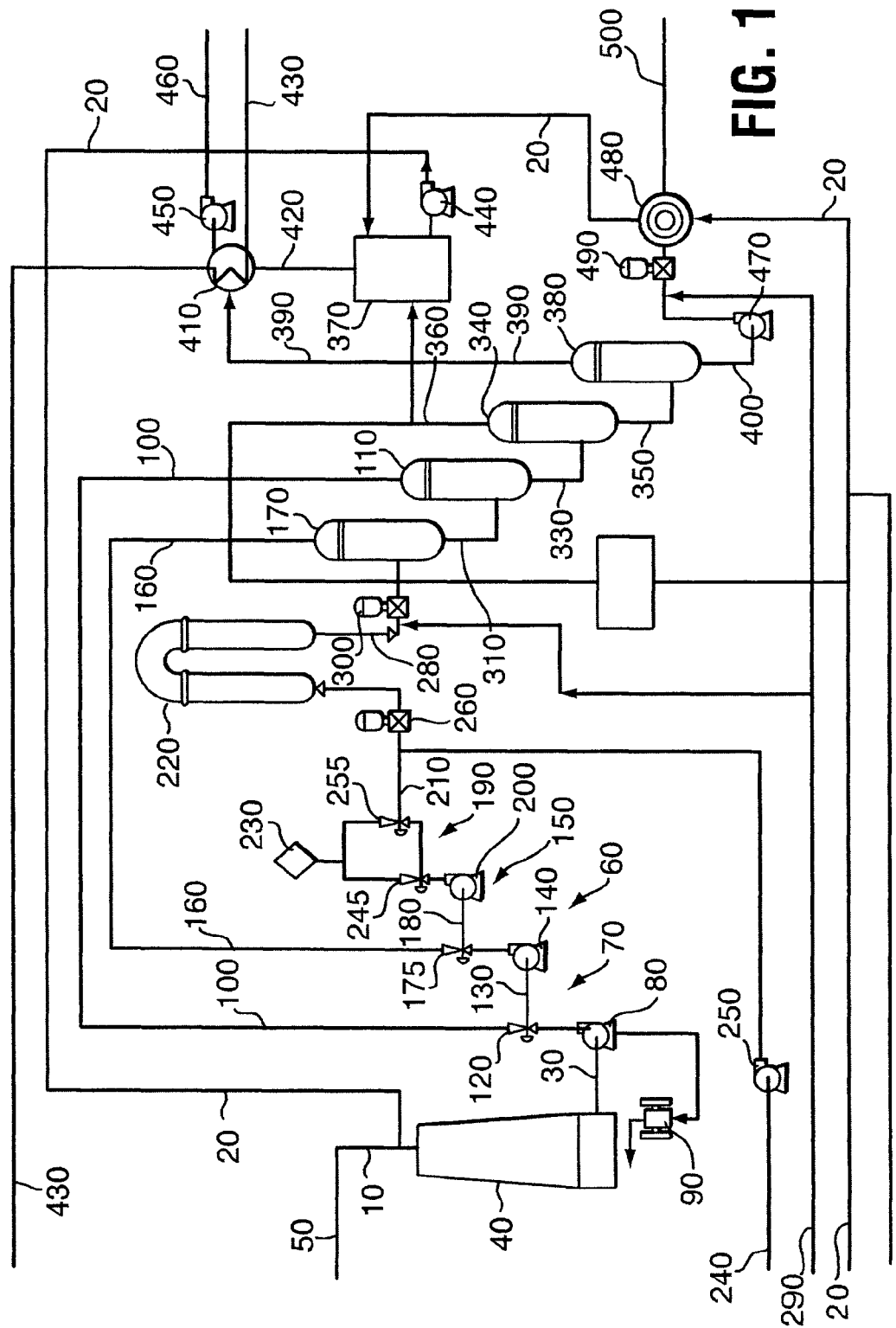
FIG. 1 is a process flow diagram illustrating the steps of processing the lignocellulosic feedstock according to an embodiment of the invention.

The following description is of preferred embodiments.

The present invention relates to a method for the continuous processing of lignocellulosic feedstocks. More specifically, the present invention provides a method for the continuous processing of lignocellulosic feedstocks by acidic pretreatment.

The following description is of an embodiment by way of example only and without limitation to the combination of features necessary for carrying the invention into effect.

According to the present invention, there is provided a method for processing lignocellulosic feedstocks which improves the economics of the process by decreasing the exposure of the equipment to harsh acidic conditions typically employed during pretreatment. By carrying out an intermediate pH adjustment of the pressurized feedstock after pretreatment and before further processing steps, process equipment downstream of the pretreatment step is less susceptible to corrosion by harsh acidic conditions typically employed. Further advantages of increasing the pH of the pressurized feedstock to the intermediate pH after pretreatment and before further processing include reductions in the amount of scale build-up on process equipment, increased sugar stability and improvements in the dispersion of the added base.

If a flashing step is carried out at the intermediate pH of between about 2.5 and about 3.5, the removal of volatile components in the pretreated feedstock is more effective than at higher pH values. If flashing is carried out at a pH above pH 4.0, removal of toxic volatile acids present in the pretreated feedstock, such as acetic acid and formic acid, is not as effective since a larger fraction of these acids would be present in the non-volatile salt form. These volatile acids inhibit subsequent processing steps. Acetic acid has a $pK_a$ of about 4.75 ($K_a$ of $1.78 \times 10^{-5}$) so that at pH 4.0, about 14.8 mole % of the acid is present in the non-volatile acetate form, which cannot be removed by flashing. At pH 3.5, only 5.6 mole % of the acid is present in the non-volatile acetate form. Formic acid has a $pK_a$ of 3.75 ($K_a$ of $1.8 \times 10^{-4}$) and therefore at pH 4.0 over half of the acid (64 mole %) would be present in the salt form (formate salt). At pH 3.5, only 36.2 mole % is present as the non-volatile formate salt.

Thus, the method of the present invention comprises adjusting the pH of the feedstock after an acidic pretreatment step to an intermediate pH range of between about pH 2.5 to about 3.5.

The process is a continuous process, with continuous feeding of feedstock and withdrawal of pretreated feedstock.

The process may be carried out prior to a step of enzymatic hydrolysis that increases the digestibility of the cellulose in the feedstock by cellulase enzymes. The cellulase enzymes convert at least a portion of the cellulose in the feedstock to glucose.

Therefore, the present invention provides a continuous process (A) for treating a lignocellulosic feedstock comprising the steps of:

a. pretreating the lignocellulosic feedstock at elevated pressure in a pretreatment reactor at a pH between about 0.4 and about 2.0 to produce a pressurized, pretreated feedstock;

b. adding one or more than one soluble base to the pressurized, pretreated feedstock after exit from the pretreatment reactor to adjust the pressurized, pretreated feedstock to an intermediate pH of between about pH 2.5 and about pH 3.5 to produce a pressurized, partially-neutralized feedstock;

c. flashing the pressurized, partially-neutralized feedstock one or more than one time at the intermediate pH to produce a flashed feedstock; and d. adjusting the pH of the flashed feedstock with one or more than one base to produce a neutralized feedstock having a pH between about 4 and about 6.

There is also provided a continuous process (B) for providing a processed lignocellulosic feedstock comprising the steps of:

a. pretreating the lignocellulosic feedstock at elevated pressure in a pretreatment reactor at a pH between about 0.4 and about 2.0 to produce a pressurized, pretreated lignocellulosic feedstock;

b. adding one or more than one soluble base to the pressurized, pretreated lignocellulosic feedstock after exit from the pretreatment reactor to adjust the pressurized, pretreated lignocellulosic feedstock to an intermediate pH of between about pH 2.5 to about pH 3.5 to produce a pressurized, partially-neutralized feedstock; and c. further processing the pressurized, partially-neutralized feedstock at the intermediate pH to produce the processed lignocellulosic feedstock.

The feedstock for the process is a lignocellulosic material. By the term "lignocellulosic feedstock", it is meant any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or more, or any amount therebetween, for example, but not limited to 20, 22, 24, 26, 28, 30, 32, 34, 36, 38, 40, 42, 44, 46, 48 and 50% (w/w) cellulose. The lignocellulosic feedstock also comprises lignin in an amount greater than about 10%, more preferably in an amount greater than about 15% (w/w). The lignocellulosic feedstock may also comprise small amounts of sucrose, fructose and starch.

Examples of preferred lignocellulosic feedstocks include (1) agricultural wastes such as corn stover, wheat straw, barley straw, canola straw, oat straw, rice straw and soybean stover; and (2) grasses such as switch grass, miscanthus, cord grass and reed canary grass.

The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill. Feedstock may be reduced to particles having a length of about 1/16 to about 1 in., or any amount therebetween; for example, the length of the particles may be about 1/16, 1/8, 3/16, 1/4, 5/16, 3/8, 7/16, 1/2, 9/16, 5/8, 11/16, 3/4, 13/16, 7/8 or 1 in., or any amount therebetween. Chemical action typically includes the use of heat (often steam), acids and solvents. Several chemical and mechanical pretreatment methods are well known in the art. The preferable equipment for the particle size reduction is a hammer mill, a refiner or a roll press as disclosed in WO 2006/026863, which is incorporated herein by reference.

The pretreatment may be employed to increase the susceptibility of the lignocellulosic feedstock to hydrolysis by cellulase enzymes. For example, the pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is designed so that complete hydrolysis of the hemicellulose and a small amount of conversion of cellulose to glucose will occur. Preferably, the pretreatment is carried out to minimize the degradation of xylose and the production of furfural. Preferably, less than about 10% of the xylan in the feedstock is converted to furfural in pretreatment and the amount of furfural produced in pretreatment is less than about 5 wt % of the amount of glucose produced in the pretreatment and enzyme hydrolysis step. The cellulose is hydrolyzed to glucose in a subsequent step that uses cellulase enzymes. During the pretreatment, typically an acid concentration from about 0.02% (w/w) to about 2% (w/w), or any amount therebetween, is used for the treatment of the lignocellulosic feedstock.

The process is a continuous process, meaning that the lignocellulosic feedstock is pumped through a reactor continuously. Continuous acid pretreatment is familiar to those skilled in the art, see for example U.S. Pat. No. 5,536,325 (Brink); U.S. Pat. No. 4,237,226 (Grethlein; which are incorporated herein by reference). Other methods that are known within the art may be used as required for continuous preparation of a pretreated feedstock, for example, but not limited to, those disclosed in U.S. Pat. No. 4,556,430 (Converse et al.; which is incorporated herein by reference).

Preferably, the feedstock is slurried in liquid prior to pretreatment. The liquid used to produce the slurry may be any suitable liquid known in the art such as water or a liquid that is miscible or immiscible with water, or a mixture thereof. The use of organic liquids in pretreatment systems is described by Converse et al., (U.S. Pat. No. 4,556,430) and has the advantage that the low boiling point liquids can easily be recovered and reused. Other pretreatments, such as the Organosolv™ process, also use organic liquids. In the case where an organic liquid is used to slurry the feedstock, the liquid may be recovered in a flashing step and recycled to the slurry point or a heating train for reuse.

The feedstock may be slurried at a temperature of between about 40° C. and about 100° C., or any temperature range therebetween; for example, the feedstock may be at about 40, 45, 50, 55, 60, 65, 70, 75, 80, 85, or 90° C., or any temperature therebetween. The hot water may be recirculated from elsewhere in the process, or heated immediately prior to addition of the feedstock.

FIG. 1 is included as an example of how the present invention could be practised and is not meant to be limiting; various combinations of the process equipment shown are possible as would be known to one skilled in the art. The feedstock 10 may be slurried with water 20, for example heated water, to produce a feedstock slurry 30. Without being limiting, the water 20 and feedstock 10 can be combined in a drop leg 40 or other suitable means including a soaking tank. Optionally, prior to preparing the slurry 30, the feedstock 10 may be leached 50 with water to remove inorganic salts and other soluble compounds.

The heated water can be re-circulated from elsewhere in the process (see FIG. 1) or heated immediately prior to addition to the feedstock. Adding additional water by re-circulation may aid in the pumping of the feedstock, particularly with an MC® (medium consistency) pump or other pump suitable for handling a medium consistency slurry. The optimal amount of water depends on the physical properties of the feedstock and can be ascertained by one of skill in the art. Excess quantities of water will result in additional heat requirements and reduce the efficiency of the process, while quantities that are too small will be absorbed by the feedstock and impact pumpability.

The pretreatment temperature will generally depend on the retention time, acid concentration, feedstock used and degree of treatment required; the pretreatment temperature is generally between about 160° C. and about 280° C., or any temperature therebetween. For example, the temperature may be about 160, 165, 170, 175, 180, 185, 190, 195, 200, 205, 210, 215, 220, 225, 230, 235, 240, 245, 250, 255, 260, 265, 270, 275, or 280° C.

The concentration of the slurry entering the pretreatment system is about 4% to 32% (w/w) feedstock solids, or any amount therebetween. The condensation of steam in the heating of the slurry decreases the solids concentration to about 80% of its initial value. Thus, the feed to the pretreatment reactor is typically about 3% to about 27% (w/w) feedstock solids, or any amount therebetween.

The pretreatment is carried out at elevated pressure to produce a pressurized, pretreated feedstock. By the expression "elevated pressure", it is meant that the pressure during pretreatment is between about 50 and about 700 psig or between about 75 and about 600 psig, or any pressure range therebetween. For example, the pretreatment may be carried out at 50, 100, 75, 150, 200, 250, 300, 350, 400, 450, 500, 550, 600, 650 or 700 psig, or any amount therebetween.

The feedstock may be heated with steam during pretreatment. In a non-limiting example, one method to carry this out is to use low pressure steam to partially heat the feedstock, which is then pumped to a heating train of several stages.

An alternative to pumping the feedstock directly into a heating train is to leach the salts, proteins, and other impurities out of the feedstock, as taught by Griffin et al. in WO 02/070753 (incorporated herein by reference). Without being limiting, the feedstock may then be pumped into the heating train.

The heating train typically comprises at least one stage of steam heating of the feedstock, with subsequent heating stages employing successively higher temperatures. In a non-limiting example, about 2 to 8 stages, or any amount therebetween, may be used; for example 2, 3, 4, 5, 6, 7 or 8. Preferably, the number of stages is high enough to provide the ability to use steam at the different pressures that are available, but low enough so the cost of pumps and the complexity is reasonable.

The following is a non-limiting example of how the feedstock may be heated in a heating train. With reference to FIG. 1, the feedstock slurry 30 may be transferred to a first stage 70 of the heating train 60 by, for example, a first transfer pump 80. The first transfer pump 80 may, for example, be connected to a first vacuum pump 90 that de-aerates the slurry 30. Heat to the first stage 70 may be provided by direct injection of a second steam and volatiles stream 100, which may be provided by a second flash tank 110, which is described in more detail below. Without being limiting, the steam may be directly injected into the heating stage with the use of a steam mixer, for example steam mixer 120 that is familiar to those skilled in the art (Pulp Bleaching: Principles and Practice, Reeve and Dence, p. 539-568; incorporated herein by reference). This method results in a rapid, uniform heating of the slurry, thereby minimizing degradation of the feedstock.

The resulting first stage slurry 130 may be conveyed by a second transfer pump 140 to a second stage 150 of the heating train 60. Heat may be provided by a first steam and volatiles stream 160 from a first flash tank 170, which is described in more detail below. This steam and volatiles stream 160 may be added to the first stage slurry via a second steam mixer 175 to produce a second stage slurry 180.

The second stage slurry 180 may be conveyed to a third heating stage 190 by a third transfer pump 200. The final heating stage or third heating stage 190 may involve the injection of live steam immediately prior to entry of an inlet stream 210 into a pretreatment reactor 220. For example, the slurry may be heated with live steam 230. The live steam 230 may be added via third 245 and fourth 255 steam mixers. In this non-limiting example, the steam pressure in the final heating stage is the pressure at which the saturated steam corresponds to the pretreatment temperature.

The acid may be added to the feedstock at any point prior to its entry into the pretreatment reactor. For example, the acid may be added to the drop leg 40, to the heating stages 70, 150 or 190 or just prior to its entry into the pretreatment reactor. The acid may be added in one or more locations. Preferably, the acid is added to the feedstock just prior to its entry into the pretreatment reactor to minimize corrosion of upstream equipment. Without wishing to be limiting in any manner, the acid may be added in a final heating stage of a heating train. In this case, the acid may be added immediately prior to, or immediately after the point of final live steam injection. For example, an acid 240, such as sulfuric acid, may be conveyed by an acid pump 250 to the inlet stream 210 and mixed with the feedstock in mixer 260. A preferred method to carry this out is to dilute the acid with water to a concentration of about 10% (w/w) of pure acid in the acid stream by using a mixing tee or similar device and adding the diluted acid directly to the inlet stream 210.

Examples of acids that can be used in the process include those selected from the group consisting of sulfuric acid, sulfurous acid, sulfur dioxide and a combination thereof. The preferred acid is sulfuric acid. The acid may be stored as a 93% w/w concentrate. The amount of acid added may vary, but should be sufficient to achieve a final concentration of acid of about 0.02% to about 2% w/w, or any amount therebetween. The resulting pH of the feedstock is about pH 0.4 to about pH 2.0, or any pH range therebetween. For example, the pH of the slurry may be between about 0.4, 0.5, 0.6, 0.7, 0.8, 0.9, 1.0, 1.1, 1.2, 1.3, 1.4, 1.5, 1.6, 1.7, 1.8, 1.9, or 2.0, or any amount therebetween.

As would be appreciated by one of skill in the art, measurement of pH presents a challenge at the elevated temperature and pressure of a pretreatment system and pH probes at these conditions are not reliable. For the purpose of this specification, the pH of pretreatment is the pH value measured by adding acid and water (and other liquids if present) to the feedstock at a temperature of 25° C. at the concentrations present at the entrance to the pretreatment reactor.

The pretreatment reactor may be a cylindrical pipe to convey a plug flow of feedstock slurry through it. The retention time in the pretreatment reactor will vary depending on the temperature, acid concentration, feedstock used, and the degree of treatment desired. For example, the slurry could be retained in the pretreatment reactor for about 0.05 to about 10 minutes, or any time therebetween; for example, the retention time may be about 0.05, 0.1, 0.5, 1, 1.5, 2, 2.5, 3, 3.5, 4, 4.5, 5, 5.5, 6, 6.5, 7, 7.5, 8, 8.5, 9, 9.5, or 10 minutes. Preferably, most of the hemicellulose in the feedstock and a small amount of the cellulose is hydrolyzed, with minimal degradation of the monomeric sugars.

The pretreatment reactor may be designed to maintain a uniform or a plug flow of the feedstock. Preferably, there is minimal channeling of solids or liquid. If steam is used, a valve may be used at the exit of the pretreatment reactor to maintain a back pressure necessary to maintain the steam pressure at the desired level.

After exiting the pretreatment reactor, the feedstock is still pressurized. By the expression "pressurized, pretreated feedstock", it is meant that the pretreated feedstock has a pressure of between about 50 and 700 psig, or any amount therebetween.

The pH of the pretreated feedstock is next adjusted to the intermediate pH of between about pH 2.5 and about 3.5 with a soluble base to produce a partially-neutralized feedstock. This step may be carried out immediately or shortly after the pretreated slurry exits the pretreatment reactor. For example, the base may be added prior to entry of the pretreated feedstock into a flash tank. A non-limiting example of this is depicted in FIG. 1 in which base 190 is added to the pretreated slurry 280 by a mixer 300 prior to entry into a first flash tank 170. The intermediate pH adjustment may also be carried out after a step of partial depressurization as described in more detail below.

After the intermediate pH adjustment, the feedstock is still pressurized. By the expression "pressurized, partially-neutralized feedstock", it is meant that the partially-neutralized feedstock has a pressure of between about 50 and about 700 psig. For example, the pretreated feedstock or partially-neutralized feedstock may have a pressure of 50, 75, 100, 150, 200, 250, 300, 350, 400, 450, 500, 550, 600, 650 or 700 psig, or any amount therebetween.

The intermediate pH adjustment may be performed after one or more than one step of partial depressurization. The partial depressurization may involve one or more than one step of flashing so that the pressure of the pretreated feedstock is reduced. By partially depressurizing the pretreated feedstock, the soluble base may be handled with greater ease at the lower pressures.

By the term "partial depressurization", it is meant that the pretreated feedstock is depressurized by at least 50 psig from the pretreated pressure, but remains above the pressure of a final depressurization stage.

The intermediate pH is between about pH 2.5 and about pH 3.5, or any range therebetween, for example, the pH may be adjusted to pH 2.5, 2.6, 2.7, 2.8, 2.9, 3.0, 3.1, 3.2, 3.3, 3.4, 3.5, or any pH therebetween.

The intermediate pH of between about 2.5 and about 3.5 is high enough to limit corrosion of the equipment and improve the stability of the sugars, while being low enough to minimize salt precipitation thereby reducing scale deposition. When a flashing step is carried out, the intermediate pH is low enough to enable flashing of volatile organic acids.

Any suitable soluble base may be used to adjust the pH to the intermediate pH. For example, the base used for adjustment to the intermediate pH may be selected from the group consisting of ammonia, ammonium hydroxide, sodium hydroxide, potassium hydroxide, potassium carbonate, potassium bicarbonate, sodium carbonate, sodium bicarbonate or mixtures thereof. Preferably, the soluble base is selected from the group consisting of ammonia, ammonium hydroxide and sodium hydroxide.

By the term "soluble base", it is meant a base that has a solubility in water that is at least 0.1 M at 20° C. This term is meant to exclude salts or gases that are slightly soluble or insoluble. Examples of bases that are excluded are $CaCO_3$ and $Ca(OH)_2$. The term "base" is meant to encompass any species that, when dissolved in water, gives a solution with a pH that is more than 7 and which is suitable for adjusting the pH of the pretreated feedstock to between about 2.5 and about 3.5. It would be understood by a person of skill in the art that the dissolution of gases, such as ammonia, in water can require maintaining a pressure higher than atmospheric. It should be appreciated, however, that insoluble bases can be utilized during an over-liming process. As described in more detail below, over-liming is an optional treatment that may be carried out on the partially-neutralized feedstock prior to adjustment to a pH suitable for enzymatic hydrolysis.

In most cases, the soluble base is stored as a solution in water and added to the slurry at an appropriate concentration. As would be known by those of skill in the art, the concentration of the base prior to its addition to the slurry may be determined based on the concentration of the commercial base, the capacity of the pumping system, and the ability to achieve an even dispersion of the base into the slurry. Preferably, the soluble base is at a concentration of about 20% to about 50% (w/w) when it is added to the slurry, or any amount therebetween; for example, the base may be added at a concentration of 20%, 25%, 30%, 35%, 40%, 45%, or 50% (w/w), or any amount therebetween.

In the case of gases, the base can be stored as a gas, liquid or as a solution in water. One example of this is ammonia, which can be stored as ammonia gas or liquid or as ammonium hydroxide in water.

If the soluble base is not volatile, it may be conveyed to the pretreated feedstock by a pipe and heated, by steam or other means, prior to addition to the pretreated feedstock. The soluble base may be heated to a temperature of between about 150° C. and 250° C., or any amount therebetween; for example, the temperature may be 150° C., 170° C., 190° C., 210° C., 230° C., or 250° C., or any temperature therebetween. Alternatively, the soluble base may be added with prior heating, and heated by contact with the slurry.

If the base is a volatile aqueous solution, such as ammonium hydroxide, it may be added to the slurry according to the method described above for adding non-volatile bases. However, those skilled in the art will recognize that heating a volatile aqueous solution to high temperatures causes a high pressure to build up, which can be a hazard or require specialized equipment. An alternative method of adding a volatile aqueous base is to heat the aqueous solution with steam or by other means to reach a desired temperature, and flash it, thereby creating a vapor phase that is rich in the base and an aqueous phase. The heated, high-pressure vapor can then be added to the process stream without overly increasing the pressure of the system.

If the base is stored as a gas, such as ammonia, it may be added directly to the slurry.

A non-limiting example of a method of adding the base ammonium hydroxide is provided in Example 4, in which case ammonium hydroxide is added at a concentration of about 30% (w/w), heated with steam to reach a temperature of about 185° C., and then flashed and injected into the feedstock slurry to reach a pH of between about 2.5 and 3.0.

The intermediate pH can be measured directly using a pH probe if the temperature of the feedstock is below about 105° C. If the feedstock is above this temperature and a probe is not available which operates at this point in the process, the pH can be measured further downstream where the feedstock is cool enough to be compatible with the pH probe.

After the intermediate pH adjustment, further processing of the partially-neutralized feedstock is carried out. By the term "further processing", it is meant processing steps that are typically performed after pretreatment to depressurize and/or cool the feedstock. This may include, but is not limited to flashing by rapid depressurization to cool down the pretreated feedstock and remove steam and volatiles, or venting. After depressurizing or cooling, the feedstock may be adjusted to a pH that is amenable for enzymatic hydrolysis, such as a pH of about 4-6 as described below.

Preferably, the pressurized, partially-neutralized feedstock or the partially depressurized, partially-neutralized feedstock is flashed. One or more than one flash stage may be carried out. The preferred number of flash stages is 2 to 8; for example 2, 3, 4, 5, 6, 7, or 8 flash stages may be performed.

As described previously, the flashed steam may be sent to a heating train for heating the feedstock prior to the pretreatment. Steam recovery may be carried out as described in WO 2006/034590 (which is incorporated herein by reference).

The following is a non-limiting example of how the flashing may be carried out. Referring again to FIG. 1, if a series of flash tanks are employed, the pretreated slurry 280 may be flashed in a first flash tank 170 to produce a steam and volatiles stream 160 and a first flash tank slurry 310. As described previously, the first steam and volatiles stream 160 may optionally be used to heat the second stage 150 of the heating train 60.

The first flash tank slurry 310 may be flashed in a second flash tank 110 to produce a second flash tank slurry 330 and the second steam and volatiles stream 100. As described above, the second steam and volatiles stream 100 may be used to heat the first stage 70 of the heating train 60.

The second flash tank slurry 330 may be flashed in a third flash tank 340 to produce a third flash tank slurry 350 and a third steam and volatiles stream 360. A portion of the third steam and volatiles stream 360 may be sent to a sparger tank 370. The remaining portion may be used as a source of low pressure steam for the plant.

The third flash tank slurry 350, may be flashed in a fourth flash tank 380 to produce a fourth steam and volatiles stream 390 and a fourth flash tank slurry 400. The steam and volatiles stream 390 may be condensed with a beat exchange condenser 410 and added, for example, to the sparger tank 370 via line 420. Condenser fluid supplied to the heat exchange condenser 410 may be boiler water feed 430 which is heated. A second vacuum pump 450 may remove non-condensibles 460 to atmosphere.

The fourth flash tank slurry 400 may be pumped by a fourth transfer pump 470 to a heat exchanger 480. Without being limiting, prior to the point at which the fourth flash tank slurry 400 enters the heat exchanger 480, a base 290 may be injected into the slurry 400 by a mixer 490 to adjust the pH up to about 4.0 to about 6.0. Process water stream 20 may be the fluid for the heat exchanger 480. The process water stream 20 exiting the heat exchanger 480 may be added to the sparger tank 370, where it is heated, for example, by hot water streams via line 420. The process water stream 20 may also be heated by steam from the third flash tank 340. The hot water from the sparger tank 370 may be conveyed by a hot water pump 440 to the drop leg 30 where it may be used to slurry the feedstock 10.

If an organic liquid is used to slurry the feedstock, the liquid may be recovered by flashing and sent to an original slurry point or a heating train for reuse with the feedstock.

The intermediate pH adjustment and the processes that may take place at this pH, such as flashing of the steam, are followed by adjusting the pH of the feedstock to a value which is suitable for a subsequent step of enzymatic hydrolysis to produce a neutralized feedstock. The pH value is optimal for the enzyme used.

The pH adjustment prior to enzymatic hydrolysis is carried out to reach a pH of about 4.0 to about 6.0, or any pH range therebetween, or between about pH 4.0 to about pH 5.5, or any pH range therebetween, or between about pH 4.5 to about pH 5.5 or any pH range therebetween. For example, the pH may be adjusted to about 4.0, 4.2, 4.4, 4.6, 4.8, 5.0, 5.2, 5.4, 5.6, 5.8 or 6.0.

These are the optimal pH ranges for cellulase enzymes. The pH can be higher or lower than about pH 4.5 to about 5.5 if the cellulase enzymes used are alkalophilic or acidophilic, respectively. It remains that the pH of the feedstock should be adjusted to within the range of optimum pH for the enzymes used. For the pH adjustment, any suitable alkaline solution known in the art can be used. This includes bases selected from the group consisting of ammonia, lime, calcium hydroxide, potassium hydroxide, magnesium hydroxide, sodium hydroxide potassium carbonate, potassium bicarbonate, sodium carbonate, sodium bicarbonate and a mixture thereof. Preferably, the base is selected from the group consisting of ammonia, ammonium hydroxide and sodium hydroxide.

Alternatively, prior to adjustment to a pH that is suitable for enzymatic hydrolysis, a pH adjustment can be carried out in which the pH of the feedstock is higher than that used for enzymatic hydrolysis. The pH can be subsequently adjusted down to the range for enzymatic hydrolysis. One example of this is to carry out an over-liming process, in which the pH of the feedstock would be adjusted to about pH 11 with the addition of lime after exiting the pretreatment reactor. After adjustment to this pH, a subsequent pH adjustment suitable for enzymatic hydrolysis (e.g. a pH of about 4.0 to about 6.0) would be reached with the addition of phosphoric acid or any other suitable acid.

Optionally, any suitable number of pH changes can be carried out after the adjustment to the intermediate pH provided the final pH is at a pH suitable for enzymatic hydrolysis. The choice of these further pH adjustments depends on maintaining the stability of sugars present, avoiding corrosion of the process equipment and minimizing the build up of scale.

For adjustment to the intermediate pH or further pH adjustments, if the pH is to be adjusted upward, this may be accomplished with a base selected from the group consisting of sodium hydroxide, potassium hydroxide, ammonia, ammonium hydroxide, magnesium hydroxide, potassium carbonate, potassium bicarbonate, sodium carbonate and sodium bicarbonate, or any combination thereof. Preferably, the pH is adjusted with ammonia, ammonium hydroxide or sodium hydroxide. If the pH is to be adjusted downward, this can be carried out with any suitable acid, including but not limited to sulfuric acid, phosphoric acid or sulfurous acid.

The slurry may also be cooled to the optimum temperature for enzymatic hydrolysis, which may be carried out using a heat exchanger. For example, with reference to FIG. 1, the hydrolysis slurry 500 may be cooled by a heat exchanger 480. The slurry is cooled to about 30° C. to about 70° C., the temperature range depending on the cellulase enzyme used. Generally, a temperature in the range of about 45° C. to about 55° C., or any temperature therebetween, is suitable for most cellulase enzymes; for example, the temperature may be about 45, 46, 47, 48, 49, 50, 51, 52, 53, 54, or 55° C. However, the temperature may be higher for thermophilic cellulase enzymes. For example, but without wishing to be limiting, the slurry is cooled to about 50° C. for hydrolysis performed with cellulase enzymes. A non-limiting example of a cellulase enzyme mixture may be made by the fungus *Trichoderma*.

By the term "cellulase enzymes", "cellulase", or "enzymes", it is meant enzymes that catalyze the hydrolysis of cellulose to products such as glucose, cellobiose, and other cello-oligosaccharides. Cellulase is a generic term denoting a multienzyme mixture comprising exo-cellobiohydrolases (CBH), endoglucanases (EG) and β-glucosidases (βG) that can be produced by a number of plants and microorganisms. The process of the present invention can be carried out with any type of cellulase enzymes, regardless of their source. Among the most widely studied, characterized and commercially produced cellulases are those obtained from fungi of the genera *Aspergillus, Humicola,* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least 4 EG enzymes.

Cellulase enzymes work synergistically to hydrolyze cellulose to glucose. CBHI and CBHII generally act on the ends of the glucose polymers in cellulose microfibrils liberating cellobiose (Teeri and Koivula, 1995, Carbohydr. Europe 12, 28-33) while the endoglucanases act at random locations on the cellulose. Together, these enzymes hydrolyze cellulose to smaller cello-oligosaccharides such as cellobiose. Cellobiose is hydrolyzed to glucose by β-glucosidase.

The cellulase enzyme dosage is chosen to achieve a sufficiently high level of cellulose conversion. For example, an appropriate cellulase dosage can be about 5.0 to about 100.0 Filter Paper Units (FPU or IU) per gram of cellulose, or any amount therebetween. For example, the cellulase dosage may be about 5, 8, 10, 12, 15, 18, 20, 22, 25, 28, 30, 32, 35, 38, 40, 42, 45, 48, 50, 60, 70, 80, 90, or 100 FPU, or any amount therebetween. The FPU is a standard measurement familiar to those skilled in the art and is defined and measured according to Ghose (1987, Pure and Appl. Chem. 59:257-268). An adequate quantity of β-glucosidase (cellobiase) activity is also added to the mixture. The dosage level of β-glucosidase may be about 5 to about 400'-glucosidase units per gram of cellulose, or any amount therebetween, or from about 35 to about 100'-glucosidase units per gram of cellulose; for example, the dosage may be 35, 40, 45, 50, 55, 60, 65, 70, 75, 80, 85, 90, 95, 100, 125, 150, 175, 200, 225, 250, 275, 300, 325, 350, 375, or 400 β-glucosidase units per gram of cellulose, or any amount therebetween. The β-glucosidase unit is measured according to the method of Ghose (supra).

The enzymatic hydrolysis continues for about 24 hours to about 250 hours, or any amount of time therebetween, depending on the degree of conversion desired. For example, the reaction time could be about 24, 30, 40, 50, 60, 70, 80, 90, 100, 120, 130, 140, 150, 160, 170, 180, 190, 200, 210, 220, 230, 240 or 250 hours, or any amount therebetween. The resulting slurry is an aqueous solution of glucose and xylose with lignin and other unconverted, suspended solids. The sugars are readily separated from the suspended solids and may be further processed as required, for example, but not limited to, fermentation to ethanol by yeast.

In another non-limiting example of the present invention, a two-stage pretreatment system may be used. In the first stage, the acidified feedstock is heated in a heating train to a temperature below about 170° C. The feedstock is then reacted at about 170° C. in the presence of about 0.5% to about 3% acid to hydrolyze the hemicellulose prior to the main pretreatment reaction. The solubilized hemicellulose can optionally be washed away from the slurry with water, thereby preventing degradation of the sugar in the second stage of pretreatment. The remaining feedstock is then subjected to the second stage of pretreatment involving the conditions outlined above. For example, the second stage of pretreatment may involve pumping the feedstock through a heating train of one or more than one heating stages, each heating stage including a pump to increase stage pressure and a direct steam injection to heat the feedstock slurry. The acid is added to provide an acid concentration of 0.2% to 2% (w/w) to produce a heated, acidified feedstock slurry. The heated, acidified feedstock slurry is subsequently passed through a pretreatment reactor at a temperature of 160° C. to 280° C. for a time sufficient to increase the efficiency of conversion of cellulose in the feedstock to glucose using cellulase enzymes. After the slurry exits the pretreatment reactor, the pH is adjusted to between about 2.5 and 3.5 using ammonium hydroxide or other soluble base. It may then be cooled using flashing stages at successively lower pressures, without intermittent increases in pressure, and the steam energy from the flashing stages, at or near its flash temperature, may be used to heat the feedstock slurry in the heating train.

The present invention will be further illustrated in the following examples. However, it is to be understood that these examples are for illustrative purposes only, and should not be used to limit the scope of the present invention in any manner.

EXAMPLES

Example 1

The Pretreatment of Lignocellulosic Feedstock

In this non-limiting example, wheat straw is used as the feedstock (e.g. 10, FIG. 1). The feedstock may be prepared by a shearing or crushing operation, such as hammer-milling, to produce small particles, preferably <⅛ inch pieces. The feedstock is conveyed at a flow rate of about 70,000 kg/hr (dry basis), is slurried, for example in a drop leg 40, with a process water stream 20. The process water stream 20 is at a temperature of about 93° C. and is flowing at 370,000 kg/hr. The resulting feedstock slurry 30 has a solids content of 14.4% by weight. Prior to preparing the slurry 30, the feedstock 10 may be leached 50 to remove inorganic salts.

The feedstock slurry 30 is conveyed by a first transfer pump 80 to a first stage 70 of a heating train 60. First transfer pump 80 is preferably a MC® (medium consistency) pump to handle the thick slurry. The first transfer pump 80 may be connected to a first vacuum pump 90 that de-aerates the slurry 30. The heat to the first stage 70 may be provided by direct injection of second steam and volatiles stream 100 provided by a second flash tank 110, which is described in more detail below. This steam and volatiles stream 100, which is at a temperature of about 166° C. and flowing at a rate of 32,200 kg/hr, is added to the feedstock slurry 30 via a first steam mixer 120. The feedstock slurry 30 is heated by steam and volatiles stream 100 to about 131° C. to produce a first stage slurry 130.

The first stage slurry 130 is conveyed by a second transfer pump 140 to a second stage 150 of the heating train 60. Heat is provided by a first steam and volatiles stream 160 from a first flash tank 170, which is described in more detail below. This steam and volatiles stream 160 has a temperature of about 192° C. and is injected at a rate of 37,300 kg/hr into the first stage slurry to heat it to 168° C. via a second steam mixer 175 to produce a second stage slurry 180.

The second stage slurry 180 is conveyed to a third heating stage 190 by a third transfer pump 200. The second stage slurry 180 is heated to about 196° C. to about 220° C. with live steam 230 at 450 psig to create an inlet stream 210. The live steam 230 is added at a rate of 32,000 kg/hr via third 245 and fourth 255 steam mixers. The inlet stream 210 at this stage is about 11% feedstock solids. At this point, concentrated sulfuric acid (typically 93%) 240 is conveyed by acid pump 250 to the slurry through an acid mixing tee with water in an amount to reach a concentration of about 8.5% acid by weight to bring the pH to 1.4. The dilute sulfuric acid is added at a rate of 53,940 kg/hr to reach a concentration of about 0.71% (w/w).

The inlet stream 210 is next conveyed to a pretreatment reactor 220. The pretreatment reactor 220 is a cylindrical pipe to convey a plug flow of feedstock slurry through it. The inlet stream 210 flows through the pretreatment reactor 220 in approximately 10 seconds to two minutes. This is sufficient to solubilize most of the hemicellulose in the feedstock 10 and a small amount of the cellulose, with minimal degradation of the monomeric sugars, to produce a pretreated slurry 280.

Upon exiting the pretreatment reactor 220, the pretreated slurry 280 is at pH 1.4. The pretreated slurry 280 is at this pH for less than 10 seconds at which point the pH is adjusted to pH 3.0 using ammonia 290, which is added by a first ammonia mixer 300. The pretreated slurry 280 is then flashed from 368 psig to 175 psig in the first flash tank 170 to produce the steam and volatiles stream 160 and a first flash tank slurry 310. As described above, the first steam and volatiles stream 160 is used to heat the second stage 150 of the heating train 60.

The first flash tank slurry 310 is flowing at a rate of 588,000 kg/hr and is flashed from 175 to 65 psig in a second flash tank 110 to produce a second flash tank slurry 330 and the second steam and volatiles stream 100. The steam and volatiles stream 100 is flowing at a rate of 32,200 kg/hr. As described above, the second steam and volatiles stream 100 is used to heat the first stage 70 of the heating train 60.

The second flash tank slurry 330 is flowing at a rate of 555,600 kg/hr and is flashed from about 68 psig to about 45 psig in a third flash tank 340 to produce a third flash tank slurry 350 and a third steam and volatiles stream 360. The third steam and volatiles stream 360 is flowing at a rate of 8950 kg/hr and is at a temperature of 121° C. About 20% of the third steam and volatiles stream 360 is sent to a sparger tank 370. The remaining 80% is used as a source of low pressure steam for the plant.

The third flash tank slurry 350, which is flowing at a rate of 509,500 kg/hr, is flashed from about 45 psig to about 6 psig in a fourth flash tank 380 to produce a fourth steam and volatiles stream 390 and a fourth flash tank slurry 400. The fourth flash tank slurry 400 is flowing at a rate of about 499,000 kg/hr. The fourth steam and volatiles stream 390 is flowing at a rate of about 10,500 kg/hr and is at a temperature of about 110° C. The steam and volatiles stream 390 is condensed with a heat exchange condenser 410 and added to the sparger tank 370 via line 420. Condenser fluid supplied to the heat exchange condenser 410 is boiler water feed 430 which is heated. A second vacuum pump 450 removes non-condensibles 460 to atmosphere.

The fourth flash tank slurry 400, which is at a temperature of about 110° C. and is flowing at a rate of 499,000 kg/hr, is pumped by a fourth transfer pump 470 to a heat exchanger 480. Prior to the point at which the fourth flash tank slurry 400 enters the heat exchanger 480, ammonia 290 is injected into the slurry 400 by a second ammonia mixer 490 to adjust the pH up to 4.5 to 5.5. Process water stream 20 is the fluid for the heat exchanger 480. The process water stream 20 exiting the heat exchanger 480 is added to the sparger tank 370, where it is heated by hot water streams via line 420 and steam from the third flash tank 340. The hot water from the sparger tank 370 is conveyed by a hot water pump 440 to the drop leg 40 where it is used to slurry the feedstock 10.

The hydrolysis slurry 500 is at a temperature of about 70° C. The hydrolysis slurry 500 is then cooled to about 50° C. and subsequently subjected to enzymatic hydrolysis.

Example 2

Adjustment of pH of Sulfuric Acid to Decrease Corrosion of Stainless Steel

The effect of pH on the rate of corrosion of stainless steel was measured by incubating solutions of 1% sulfuric acid at various pH values in small bombs. The bombs were made of 304 stainless steel and 316 stainless steel, with compositions listed in Table 1.

TABLE 1

| | Composition of stainless steel | |
|---|---|---|
| Metal (element) | 304 stainless steel (%) | 316 stainless steel (%) |
| Iron | 68-72 | 63-70 |
| Manganese | 2 | 2 |
| Chromium | 18-20 | 16-18 |
| Nickel | 8-10 | 10-14 |
| Molybdenum | 0 | 2-3 |

The incubations were carried out for 7.5 hr at 200° C. at a mass of 250 grams. After the incubations, the degree of corrosion was measured, and the results are shown in Table 2. Increasing the pH from 1.05 to 2.06 decreased the rate of corrosion by over 98% for both 316 and 304 stainless steel. Increasing the pH to 3.24 further decreased the rate of corrosion to a level that was reduced by more than 99.7% relative to the natural 1% sulfuric acid solution.

TABLE 2

Rate of corrosion of 304 and 316 stainless steel (7.5 hr exposure at 200° C.)

| | 316 stainless | | 304 stainless | |
|---|---|---|---|---|
| pH | Thousandths of an inch | Percent reduction compared with 1% sulfuric | Thousandths of an inch | Percent reduction compared with 1% sulfuric |
| 1.05 (1% sulfuric acid) | 0.2488 | — | 0.112 | — |
| 2.06 | 0.00169 | 99.32 | 0.001517 | 98.65 |
| 3.24 | 0.00059 | 99.76 | 0.0000428 | 99.96 |

The effect of pH on mineral solubilization of 304 stainless steel and 316 stainless steel is shown in Tables 3 and 4, respectively. Significantly more material is dissolved from 304 stainless steel at pH 2.06 than at pH 3.24. For 316 stainless steel, pH 1.88 is a marked improvement over pH 1.05. The results at pH 2.8 are better yet and result in a similar amount of mineral loss as pH 3.83.

TABLE 3

| Solubilized minerals from 304 stainless steel | | |
|---|---|---|
| Metal Element | pH 2.06 (mg/L) | pH 3.24 (mg/L) |
| Chromium | 0.6 | 0 |
| Nickel | 1.37 | 0.19 |

TABLE 3-continued

Solubilized minerals from 304 stainless steel

| Metal Element | pH 2.06 (mg/L) | pH 3.24 (mg/L) |
|---|---|---|
| Iron | 14.1 | 0.17 |
| Manganese | 0.51 | 0.11 |
| Molybdenum | 0 | 0 |
| Total | 16.58 | 0.47 |

TABLE 4

Solubilized minerals from 316 stainless steel (mg/L)

| Metal Element | pH 1.05 | pH 1.88 | pH 2.8 | pH 3.83 |
|---|---|---|---|---|
| Chromium | 168 | 0.58 | 0.09 | 0.31 |
| Nickel | 335 | 3.75 | 1.51 | 1.79 |
| Iron | 2160 | 12.4 | 2.52 | 3.39 |
| Manganese | 56.1 | 0.71 | 0.38 | 0.59 |
| Molybdenum | 0.96 | 1.1 | 1.95 | 1.53 |
| Total | 2720.6 | 18.54 | 6.45 | 7.61 |

Example 3

Pretreatment of Wheat Straw with Interim pH Adjustment Using Sodium Hydroxide

Wheat straw was received in bales measuring 3 feet by 3 feet by 4 feet. The wheat straw consisted of 60.3% carbohydrates, 18.7% lignin, 3.6% protein, 3.1% silica, and 4.9% non-silica salts. The salts included 1.2% potassium, 0.57% calcium, 0.04% sodium, 0.15% magnesium, and 0.04% phosphate. A batch of 30 tonnes of the straw was hammer-milled to ⅛ inch length and slurried in water (20; FIG. 1) at a ratio of 8 parts water to 1 part solids. The slurry was pumped through piping heated by direct injection with 350 psig steam to reach a temperature of 185° C. Once at this temperature, dilute sulfuric acid (240) was added to achieve a concentration of 0.9% acid (w/w). The heated, acidified stock was maintained at this condition for 2 minutes as it passed through a pretreatment reactor (220) having an 8 inch diameter.

At the exit of the pretreatment reactor (220), and before the slurry entered a section of pipe of 4-inch diameter, the slurry pH was adjusted to pH 2.5 to 3.0 with 30% (w/w) concentrated sodium hydroxide. The alkali was added in-line and was dispersed with an in-line mixer (300). The pH-adjusted slurry was passed through a valve in the pipe to decrease the pressure and flashed in a cyclone to drop the temperature. The valve-pressure reduction and flashing were carried out three times to drop the temperature to 75° C. A significant amount of volatile compounds, including methanol, acetaldehyde, formic acid, furfural, hydroxymethyl furfural, and acetic acid were flashed along with the steam.

The slurry was then adjusted to pH 5.0 with concentrated 30% sodium hydroxide. The final cooling of the slurry to 50° C. was carried out by heat exchange with a heat exchanger (480) with cooling water (20).

The neutralized, cooled pretreated slurry (500) was then pumped into three hydrolysis tanks, each of working volume of about 140,000 liters. The tanks are equipped with bottom-mounted eductors to mix the slurry; one of the three tanks has two side-mounted agitators. The slurry consisted of 4.5% undissolved solids, and the undissolved solids consisted of 55% cellulose. Once the hydrolysis tanks were filled or the pretreated slurry was exhausted, cellulase enzyme from *Trichoderma reesei* was added. The enzyme dosage was 25 mg protein per gram cellulose, which corresponded to a cellulase activity of 25.4 Filter Paper Units (FPU) per gram of cellulose.

The hydrolyses ran for 5 days, at which point over 90% of the cellulose was converted to glucose. The final glucose concentration was 26.0 to 28.0 g/L, with an average of 27.5 g/L.

Example 4

Pretreatment of Wheat Straw with Interim pH Adjustment Using Ammonium Hydroxide

Wheat straw was received in bales measuring 3 feet by 3 feet by 4 feet. The wheat straw consisted of 60.3% carbohydrates, 18.7% lignin, 3.6% protein, 3.1% silica, and 4.9% non-silica salts. The salts included 1.2% potassium, 0.57% calcium, 0.04% sodium, 0.15% magnesium, and 0.04% phosphate. A batch of 30 tonnes of the straw was hammer-milled to ⅛ inch length and slurried in water (20) at a ratio of 8 parts water to 1 part solids. The slurry was pumped through piping heated by direct injection with 330 psig steam to reach a temperature of 185° C. Once at this temperature, dilute sulfuric acid (240) was added to achieve a concentration of 0.9% acid (w/w). The heated, acidified stock was maintained at this condition for 2 minutes as it passed through a pretreatment reactor having a diameter of 8 inches.

At the exit of the pretreatment reactor (220), and before the slurry entered a section of pipe of 4-inch diameter, the slurry pH was immediately adjusted to pH 2.5 to 3.0 with ammonia vapor. The ammonia vapor was added by starting with a supply of Aqua-Ammonia, a commercial product that is a solution of 30% (w/w) ammonia in water. A stream of ammonium hydroxide solution is pumped through a pipe heated with steam to reach a temperature of 185° C. The heated ammonia then flashes to form a liquid phase, which is water with some ammonia dissolved, and a 350 psig ammonia vapor phase with some water in the vapour phase. The ammonia vapor was injected into the slurry to reach a pH of 2.5 to 3.0. The ammonia vapor rate is set as a ratio to the sulfuric acid addition rate.

The alkali was added in-line and was dispersed with an in-line sparger directed upstream of line mixer (300). The pH-adjusted slurry was passed through a valve to decrease the pressure and flashed in a cyclone to drop the temperature. The valve-pressure reduction and flashing were carried out three times to drop the temperature to 75° C. A significant amount of volatile compounds, including methanol, acetaldehyde, formic acid, furfural, hydroxymethyl furfural, and acetic acid were flashed along with the steam.

The final cooling of the slurry was carried out by heat exchange with a heat exchanger (480) with cooling water. The cooled slurry was then adjusted to pH 5.0 with 30% ammonium hydroxide added directly from the Aqua-Ammonia storage tank.

The neutralized, cooled pretreated slurry was then pumped into three hydrolysis tanks, each of working volume of about 140,000 liters. The tanks are equipped with bottom-mounted eductors to mix the slurry; one of the three tanks has two side-mounted agitators. The slurry consisted of 4.5% undissolved solids, and the undissolved solids consisted of 55% cellulose. Once the hydrolysis tanks were filled or the pretreated slurry was exhausted, cellulase enzyme from *Trichoderma reesei* was added. The enzyme dosage was 25 mg protein per gram cellulose, which corresponded to a cellulase activity of 25.4 Filter Paper Units (FPU) per gram of cellulose.

The hydrolyses ran for 5 days, at which point over 90% of the cellulose was converted to glucose. The final glucose concentration was 26.0 to 28.0 g/L, with an average of 27.5 g/L.

Example 5

Pretreatment of Leached Wheat Straw with Interim pH Adjustment Using Ammonium Hydroxide Wheat straw was received in bales measuring 3 feet by 3 feet by 4 feet. The wheat straw consisted of 6.4% moisture. The composition of the straw, on a dry basis, was 60.3% carbohydrates, 18.7% lignin, 3.6% protein, 3.1% silica and 4.9% non-silica salts. The inorganic cationic salts present included 1.22% potassium, 0.57% calcium, 0.04% sodium, and 0.15% magnesium. The inorganic anions were 0.10% chloride, 0.16% phosphate and 0.08% sulfate. A batch of 3,363 kg of the straw was hammer-milled to particles of ⅛ inch length. The hammer-milled straw was slurried in 70,626 liters of 65° C. water. The slurry was gravity fed into a mixed tank, where it was mixed overnight for 18 hours and maintained at 65° C. The pH was 4.9 throughout the leaching process. The slurry was then pumped to a centrifuge to separate the solids from the liquid leachate stream. The centrifuge produced a cake of 29.6% solids content.

The leachate contained 10.6% of the initial fiber solids. This was at a concentration of 4090 mg/L total dissolved solids, which included 1138 mg/L protein, 494 mg/L potassium, 67 mg/L calcium, 36 mg/L magnesium, 67 mg/L chloride, 80 mg/L sulfate, 45 mg/L phosphate, 27 mg/L sodium, 163 mg/L silica, 2010 mg/L of soluble phenolics and about 600 mg/L of unidentified substances. Other than calcium and silica, which were not removed to a significant degree, the salts were removed from the straw by leaching at a yield of 50% to 93%. The protein yield in the leachate was 72%.

The solids cake from the centrifuge was slurried in water at a ratio of 8 parts water to 1 part solids. The slurry was pumped through piping heated by direct injection with 330 psig steam to reach a temperature of 185° C. Once at this temperature, dilute sulfuric acid was added to achieve a concentration of 0.9% acid (w/w). The heated, acidified stock was maintained at this condition for 2 minutes as it passed through a pipe of 8 inches diameter.

At the exit of the pretreatment pipe, and before the slurry entered a section of pipe of 4-inch diameter, the slurry pH was immediately adjusted to pH 2.5 to 3.0 with ammonia vapor. The ammonia vapor was added by starting with a supply of Aqua-Ammonia, a commercial product that is a solution of 30% (w/w) ammonium hydroxide in water. A stream of ammonium hydroxide solution is pumped through a pipe heated with steam to reach a temperature of 185° C. The heated ammonia then flashes to form a liquid phase, which is water with some ammonia dissolved, and a 350 psig ammonia vapor phase. The ammonia vapor was injected into the slurry to reach a pH of 2.5 to 3.0. The ammonia vapor rate is set as a ratio to the sulfuric acid addition rate.

The ammonia vapor was added in-line and was dispersed with an in-line sparger. The pH-adjusted slurry was passed through a valve to decrease the pressure and flashed in a cyclone to drop the temperature. The valve-pressure reduction and flashing were carried out three times to drop the temperature to 75° C. A significant amount of volatile compounds, including methanol, acetaldehyde, formic acid, furfural, hydroxymethyl furfural, and acetic acid were flashed along with the steam.

The final cooling of the slurry was carried out by heat exchange with a heat exchanger (480) with cooling water. The cooled slurry was then adjusted to pH 5.0 with 30% ammonium hydroxide added directly from the Aqua-Ammonia storage tank.

The neutralized, cooled pretreated slurry was then pumped into three hydrolysis tanks, each of working volume of about 130,000 liters. The tanks are equipped with bottom-mounted eductors to mix the slurry; one of the three tanks has two side-mounted agitators. The slurry consisted of 4.5% undissolved solids, and the undissolved solids consisted of 55% cellulose. Once the hydrolysis tanks were filled or the pretreated slurry was exhausted, cellulase enzyme from *Trichoderma reesei* was added. The enzyme dosage was 25 mg protein per gram cellulose, which corresponded to a cellulase activity of 25.4 Filter Paper Units (FPU) per gram of cellulose.

The hydrolyses ran for 5 days, at which point over 90% of the cellulose was converted to glucose. The final glucose concentration was 26.0 to 28.0 g/L, with an average of 27.5 g/L.

Example 6

Figure 2:
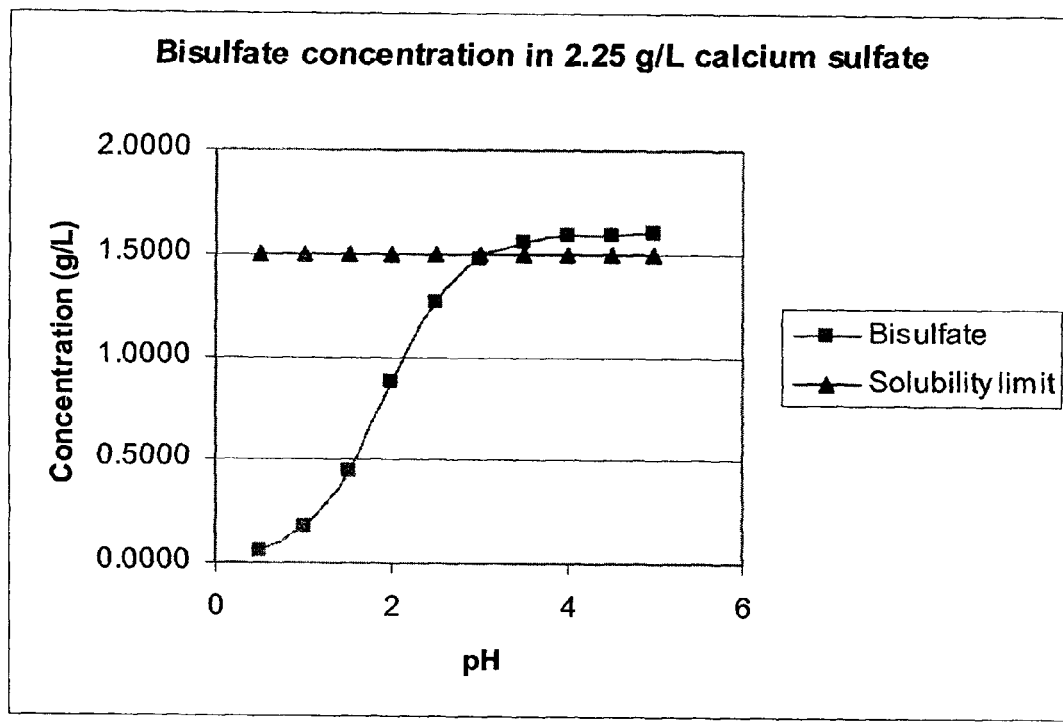
FIG. 2 depicts the concentration of sulfate (g/L) as a function of the pH after an intermediate pH adjustment.

The Concentration of Calcium Bisulfate as a Function of pH and Concentration of Calcium Sulfate The concentration of calcium bisulfate as a function of pH and concentration of calcium sulfate is shown in FIG. 2 and was determined as follows.

The calcium sulfate exists in solution at low pH as sulfuric acid ($H_2SO_4$) and as calcium bisulfate ($Ca(HSO_4)_2$). The relative fraction of calcium bisulfate is given by:

$$F = \frac{K_a}{K_a + 10^{-pH}}$$

Where
F is the fraction that is calcium bisulfate
$K_a$ is the first dissociation constant for sulfuric acid ($K_a$=0.012)
pH is the pH of the solution As the pH increases, the fraction of calcium bisulfate increases, and the fraction in the acid form decreases.

At 2.25 g/L calcium sulfate, calcium is 40/136=29.4% of the compound, and sulfate ($SO_4$) is the remaining 70.6%. The total concentration of $SO_4$ is therefore 1.59 g/L. The equation relating F to $K_a$ and pH is then used to determine the fraction that is calcium bisulfate, which is multiplied by 1.59 g/L to result in the calcium bisulfate concentrations shown in FIG. 2.

What is claimed is:

1. A continuous process for providing a processed lignocellulosic feedstock comprising the steps of:
   a. pretreating a lignocellulosic feedstock at elevated pressure in a pretreatment reactor at a pH between about 0.4 and about 2.0 to produce a pressurized, pretreated lignocellulosic feedstock;
   b. adding one or more than one soluble base to the pressurized, pretreated lignocellulosic feedstock after exit from the pretreatment reactor to adjust the pressurized, pretreated lignocellulosic feedstock to an intermediate pH of between about pH 2.5 and about pH 3.5 to produce a pressurized, partially-neutralized feedstock; and c. further processing the pressurized, partially-neutralized feedstock at the intermediate pH to produce the processed lignocellulosic feedstock.

2. The process of claim 1, wherein the step of further processing (step c.) comprises, flashing or venting the pressurized, partially-neutralized feedstock.

3. The process of claim 1, wherein the step of pretreating (step a.) is performed at a pressure between about 50 and about 700 psig.

4. The process of claim 3, wherein the step of pretreating (step a.) is performed at a pressure between about 75 and about 600 psig.

5. The process of claim 1, wherein, prior to the step of adding (step b.) and after the step of pretreating (step a.), the pressurized, pretreated feedstock is partially depressurized.

6. The process of claim 1, wherein the step of pretreating (step a.) comprises pumping the lignocellulosic feedstock through the pretreatment reactor and heating the lignocellulosic feedstock to a temperature between about 160° C. and about 280° C. with steam for a time sufficient to hydrolyze at least a portion of hemicellulose in the feedstock to produce a sugar monomer selected from the group consisting of xylose, arabinose, mannose, galactose and a combination thereof and a portion of cellulose in the feedstock to produce glucose.

7. A continuous process for treating a lignocellulosic feedstock comprising the steps of:
   a. pretreating the lignocellulosic feedstock at elevated pressure in a pretreatment reactor at a pH between about 0.4 and about 2.0 to produce a pressurized, pretreated feedstock;
   b. adding one or more than one soluble base to the pressurized, pretreated feedstock after exit from the pretreatment reactor to adjust the pressurized, pretreated feedstock to an intermediate pH of between about pH 2.5 and about pH 3.5 to produce a pressurized, partially-neutralized feedstock;
   c. flashing the pressurized, partially-neutralized feedstock one or more than one time at the intermediate pH to produce a flashed feedstock; and
   d. adjusting the pH of the flashed feedstock with one or more than one base to produce a neutralized feedstock having a pH between about 4 and about 6.

8. The process of claim 1, wherein, prior to the step of pretreating (step a.), the lignocellulosic feedstock is slurried to produce a feedstock slurry having a solids content of about 4-32% (w/w).

9. The process of claim 8, wherein the feedstock slurry is prepared in water.

10. The process of claim 8, wherein the feedstock slurry is prepared in a mixture of water and a liquid that is immiscible or miscible with water.

11. The process of claim 7, wherein the step of pretreating (step a.) is performed at a pressure between about 50 and about 700 psig.

12. The process of claim 11, wherein the step of pretreating (step a.) is performed at a pressure between about 75 and about 600 psig.

13. The process of claim 7, wherein, prior to the step of adding (step b.) and after the step of pretreating (step a.), the pressurized, pretreated feedstock is partially depressurized.

14. The process of claim 13, wherein the pressurized, pretreated feedstock is partially depressurized by one or more than one flashing step.

15. The process of claim 7, wherein the step of pretreating (step a.) comprises pumping the lignocellulosic feedstock through the pretreatment reactor and heating the lignocellulosic feedstock to a temperature between about 160° C. and about 280° C. with steam for a time sufficient to hydrolyze at least a portion of cellulose in the feedstock to produce glucose and at least a portion of hemicellulose in the feedstock to produce a sugar monomer selected from the group consisting of xylose, arabinose, mannose, galactose and a combination thereof.

16. The process of claim 7, wherein, prior to the step of pretreating (step a.), one or more than one acid selected from the group consisting of sulfuric acid, sulfurous acid, sulfur dioxide and a mixture thereof is added to the lignocellulosic feedstock.

17. The process of claim 16, wherein the acid is sulfuric acid.

18. The process of claim 7, wherein, in the step of flashing (step c.), the steam is flashed to produce flashed steam, and a portion of the flashed steam is recovered.

19. The process of claim 7, wherein, in the step of adjusting (step d), the pH of the neutralized feedstock is adjusted to between about pH 4.0 and about pH 5.5.

20. The process of claim 19, wherein the pH of the neutralized feedstock is adjusted to between about pH 4.5 and about pH 5.5.

21. The process of claim 7, wherein, in the step of adding (step b.), the one or more than one soluble base is selected from the group consisting of ammonia, ammonium hydroxide, potassium hydroxide, sodium hydroxide, potassium carbonate, potassium bicarbonate, sodium carbonate, sodium bicarbonate and a mixture thereof.

22. The process of claim 21, wherein, in the step of adding (step b.), the one or more than one soluble base is selected from the group consisting of ammonia, ammonium hydroxide and sodium hydroxide.

23. The process of claim 22, wherein, in the step of adding (step b.), the one or more than one base is ammonia.

24. The process of claim 7, wherein, in the step of flashing (step c.), the flashed feedstock is at a temperature of between about 40° C. and about 125° C.

25. The process of claim 24, wherein the flashed feedstock is at a temperature of between about 40° C. and about 100° C.

26. The process of claim 25, wherein the flashed feedstock is at a temperature of between about 50° C. and about 90° C.

27. The process of claim 7, wherein, in the step of adjusting (step d.), the one or more than one base is selected from the group consisting of ammonia, ammonium hydroxide, lime, calcium hydroxide, potassium hydroxide, magnesium hydroxide, sodium hydroxide, potassium carbonate, potassium bicarbonate, sodium carbonate, sodium bicarbonate and a mixture thereof.

28. The process of claim 7, wherein, in the step of adjusting (step d.), the one or more than one base is a soluble base.

29. The process of claim 27, wherein, in the step of adjusting (step d.), the one or more than one base is selected from the group consisting of ammonia, ammonium hydroxide and sodium hydroxide.

30. The process of claim 7, wherein the lignocellulosic feedstock is selected from the group consisting of wheat straw, barley straw, corn stover, soybean stover, canola straw, oat straw, rice straw, switch grass, cord grass, miscanthus and reed canary grass.

31. The process of claim 7, further comprising the steps of
   e. enzymatically hydrolyzing the neutralized feedstock produced in step d. to produce a sugar stream; and
   f. fermenting the sugar stream to produce ethanol.

* * * * *

UNITED STATES PATENT AND TRADEMARK OFFICE
CERTIFICATE OF CORRECTION

PATENT NO. : 7,754,457 B2
APPLICATION NO. : 11/916347
DATED : July 13, 2010
INVENTOR(S) : Brian Foody et al.

It is certified that error appears in the above-identified patent and that said Letters Patent is hereby corrected as shown below:

ON TITLE PAGE AT ITEM (57) ABSTRACT

Line 16, "truly be" should read --may be--.

COLUMN 2

Line 63, "build up" should read --buildup--.

COLUMN 3

Line 17, "build-up" should read --buildup--; and
    Line 20, "time" should read --time- --.

COLUMN 4

Line 59, "build up" should read --buildup--.

COLUMN 5

Line 1, "acid resis-" should read --acid-resis- --; and
    Line 2, "build up" should read --buildup--.

COLUMN 8

Line 19, "build-up" should read --buildup--.

COLUMN 9

Line 24, "baggase," should read --bagasse,--.

Signed and Sealed this
Twenty-second Day of March, 2011

David J. Kappos
*Director of the United States Patent and Trademark Office*

CERTIFICATE OF CORRECTION (continued)
U.S. Pat. No. 7,754,457 B2

COLUMN 16

Line 41, "build up" should read --buildup--.

COLUMN 17

Line 37, "400'-glucosidase" should read --400 β-glucosidase--; and
    Line 39, "100'-glucosidase" should read --100 β-glucosidase--.

COLUMN 22

Line 41, "vapour" should read --vapor--.

COLUMN 25

Line 45, "claim 1," should read --claim 7,--.